(12) United States Patent
El Amri et al.

(10) Patent No.: US 11,541,023 B2
(45) Date of Patent: Jan. 3, 2023

(54) COMPOUNDS AND COMPOSITIONS FOR THE TREATMENT OF NEURODEGENERATIVE AND INFLAMMATORY DISEASES

(71) Applicants: SORBONNE UNIVERSITE, Paris (FR); CENTRE NATIONAL DE LA RECHERCHE SCIENTIFIQUE, Paris (FR); INSTITUT NATIONAL DE LA SANTÉ ET DE LA RECHERCHE MÉDICALE, Paris (FR); ASSISTANCE PUBLIQUE—HÔPITAUX DE PARIS, Paris (FR); INSTITUT DU CERVEAU ET DE LA MOELLE EPINIERE, Paris (FR); UNIVERSITE DE MONTPELLIER, Montpellier (FR); ECOLE NATIONALE SUPERIEURE DE CHIMIE DE MONTPELLIER, Montpellier (FR)

(72) Inventors: Chahrazade El Amri, Ermont (FR); Feryel Soualmia, Saint-Mande (FR); Nicolas Masurier, Montpellier (FR); Sabrina Aït Amiri, Montreuil (FR); Brahim Nait Oumesmar, Paris (FR); Cyrille Deboux, Mitry Mory (FR)

(73) Assignees: SARBONNE UNIVERSITE, Paris (FR); CENTRE NATIONAL DE LA RECHERCHE SCIENTIFIQUE, Paris (FR); INSTITUT NATIONAL DE LA SANTÉ ET DE LA RECHERCHE MÉDICALE, Paris (FR); ASSISTANCE PUBLIQUE—HÔPITAUX DE PARIS, Paris (FR); INSTITUT DU CERVEAU ET DE LA MOELLE EPINIERE, Paris (FR); UNIVERSITÉ DE MONTPELLIER, Montpellier (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 197 days.

(21) Appl. No.: 16/968,890

(22) PCT Filed: Feb. 13, 2019

(86) PCT No.: PCT/FR2019/050321
§ 371 (c)(1),
(2) Date: Aug. 11, 2020

(87) PCT Pub. No.: WO2019/158859
PCT Pub. Date: Aug. 22, 2019

(65) Prior Publication Data
US 2021/0046026 A1 Feb. 18, 2021

(30) Foreign Application Priority Data
Feb. 13, 2018 (FR) ...................................... 1851206

(51) Int. Cl.
*A61K 31/167* (2006.01)
*A61P 25/28* (2006.01)

(52) U.S. Cl.
CPC ............ *A61K 31/167* (2013.01); *A61P 25/28* (2018.01)

(58) Field of Classification Search
CPC .................................................... A61K 31/167
See application file for complete search history.

(56) References Cited

PUBLICATIONS

Liang, G. et al. "Human kallikrein 6 inhibitors with a para-amidobenzylanmine P1 group identified through virtual screening" *Bioorganic & Medicinal Chemistry Letters*, 2012, pp. 2450-2455, vol. 22, No. 7.
Database Biosis [Online] Accession No. PREV200300249947, Mar. 2003, pp. 1-2, XP-002785206.
Database Biosis [Online] Accession No. PREV200800655911, Jun. 2008, pp. 1-2, XP-002785207.
Scarisbrick, I. A. et al. "Kallikreins are associated with secondary progressive multiple sclerosis and promote neurodegeneration" *Biol Chem.*, Jun. 2008, pp. 1-14, vol. 389, No. 6.
Written Opinion in International Application No. PCT/FR2019/050321, dated May 22, 2019, pp. 1-4.

*Primary Examiner* — Paul V Ward
(74) *Attorney, Agent, or Firm* — Saliwanchik, Lloyd & Eisenschenk

(57) ABSTRACT

The invention relates to compounds exhibiting kallikrein inhibitory activity, and to compositions comprising at least one of these compounds for use in the treatment of diseases or disorders in which kallikrein activity is dysregulated, particularly neurodegenerative and inflammatory diseases.

12 Claims, 5 Drawing Sheets

Compound 1

Compound 2

Figure 1:
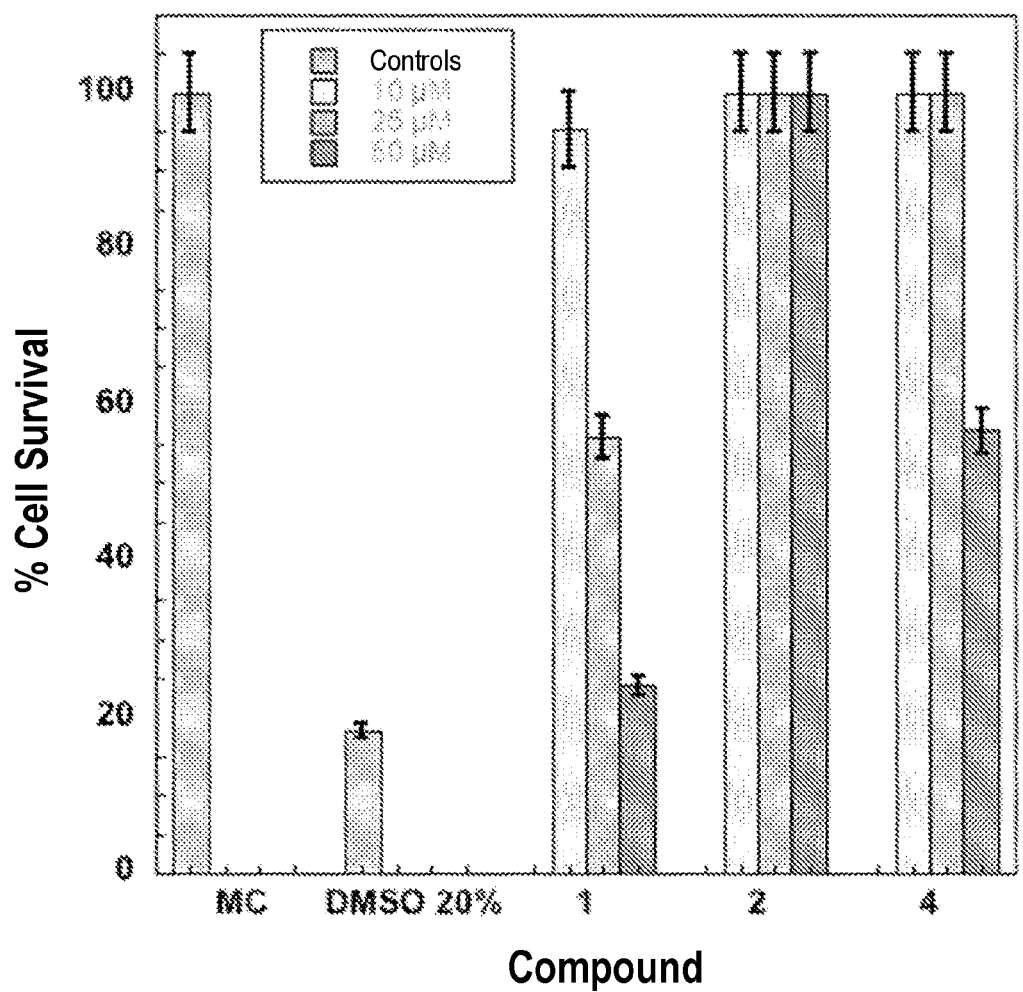

COMPOUNDS AND COMPOSITIONS FOR THE TREATMENT OF NEURODEGENERATIVE AND INFLAMMATORY DISEASES

CROSS-REFERENCE TO RELATED APPLICATION

This application is the U.S. national stage application of International Patent Application No. PCT/FR2019/050321, filed Feb. 13, 2019.

TECHNICAL FIELD OF THE INVENTION

The present invention relates to compounds exhibiting kallikrein-inhibiting activity and to compositions comprising at least one of these compounds for use in the treatment of diseases or disorders in which kallikrein activity is dysregulated, in particular neurodegenerative and inflammatory diseases.

CONTEXT OF THE INVENTION

For more than ten or so years now, the involvement of serine proteases in the central nervous system (CNS) function has been continually demonstrated. Among the relatively new serine proteases, tissue kallikreins form a family of proteases present in at least six orders of mammals. They are involved in functions as diverse as synaptic plasticity regulation, neuron survival, memory acquisition and vascular function. Among the tissue kallikreins, KLK6 (kallikrein-6 or hK6) is the most abundant in the adult CNS. It is produced by neurons and by oligodendrocytes, and has a proteolytic activity similar to that of trypsin. KLK6 thus has a broad action and a central role in the brain and the spinal cord. As a result, it is involved in pathological conditions which affect the CNS and in particular in certain neurodegenerative processes. Despite the efforts of the scientific community, very few inhibitors are available. Compounds with para-amidobenzylamine and 2-hydroxybenzamide structures exhibiting KLK6-inhibiting activity have thus been described in the article by Liang et al. ("Human kallikrein 6 inhibitors with a para-amidobenzylamine $P_1$ group identified through virtual screening", Bioorganic & Medicinal Chemistry letters, 22 (2012), 2450-2455).

Other serine proteases, namely plasmin and kallikrein 1 (KLK1), have also been described in CNS function.

These serine proteases are predominantly involved in inflammatory and neurodegenerative pathological conditions.

Among these pathological conditions, multiple sclerosis (MS) is an incurable demyelinating autoimmune disease of the CNS. This chronic disease affects more than two million individuals worldwide, including 100 000 in France with 3000 to 5000 new cases declared each year. In young adults, MS is the most common neurological disorder and also the primary cause of non-traumatic severe disability. MS is associated with an inflammatory reaction of the CNS which results in degradation of the myelin sheath surrounding the central axons and therefore, in their demyelination. This phenomenon has many consequences: (i) nerve impulse translation is impaired; (ii) neuronal suffering sets in, going as far as neurodegeneration; (iii) the myelin debris is thought to worsen the inflammation phenomenon. At the clinical level, these disruptions manifest themselves through severe motor, sensory and cognitive problems. Various studies converge towards the hypothesis that KLK6 is involved in the development of MS. It is today accepted that the patients have an abnormally high level of KLK6 in their cerebrospinal fluid (CSF). More specifically, KLK6 is thought to be involved in the various components of the pathological condition: demyelination, neuroinflammation and axonal degeneration. The excess KLK6 in patients suffering from multiple sclerosis (MS) is thought to lead to significant neuroinflammation phenomena via two different pathways, that of the PAR receptors (Protease Activated Receptors) and that of the excessive cleavage of its substrates. The drugs currently sold are fundamental treatments which target the inflammatory aspects of the pathological condition. The identification of new therapeutic compounds which act on myelin regeneration (remyelination) in MS is thus a real public health challenge. Particular effort is placed on the search for compounds capable of simultaneously treating the inflammation and the demyelination in order to give patients a more complete treatment.

The aim of the present invention is therefore to provide organic modulators of these targets, and in particular of KLK6. The present invention provides compounds which inhibit serine proteases of interest in neurodegenerative pathological conditions and inflammation, based on a para-amidobenzylamine structure. Several proteases among those which are the most important in the CNS are targeted: plasmin, tissue kallikrein (KLK1), and in particular kallikrein 6 (KLK6). The inhibitory capacity and also the spectrum of action of compounds have been evaluated and efficacious reversible KLK6 inhibitors have thus been identified. In addition, some of the compounds identified do not exhibit any toxicity with respect to primary neurons. These compounds therefore are of therapeutic interest in the neuroprotective and anti-inflammatory areas.

SUMMARY OF THE INVENTION

The present invention provides a compound for use in the treatment of a disorder or a disease linked to a dysregulation of the activity of at least one kallikrein, said compound being of formula (I) below:

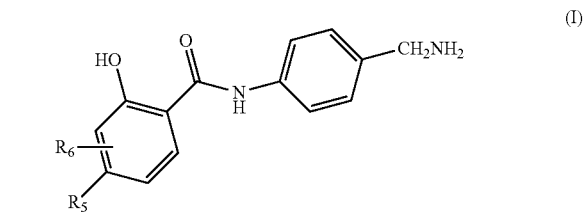

wherein:
$R_5$ represents a $(C_1-C_6)$alkyl radical and $R_6$ represents a hydrogen atom;
alternatively, $R_5$ and $R_6$ together form a ring with the two carbons of the phenyl ring to which they are attached, so as to form a naphthyl group, optionally substituted with at least one halogen atom, or an OH, $(C_1-C_6)$alkyl, $(C_1-C_6)$alkoxy, —C(O)$_2$R, or —N(R)C(O)R' radical, wherein R and R' are independently a hydrogen atom or a $(C_1-C_6)$alkyl radical,
it being possible for the amine function to have an amino protective group,
or a pharmaceutically acceptable salt thereof.

The present invention also provides compositions, in particular pharmaceutical compositions, comprising at least one compound of formula (I), in a pharmaceutically acceptable support, optionally in combination with at least one other therapeutic active agent.

It also relates to the use of at least one compound of formula (I) for preparing a pharmaceutical composition intended for treating a disorder or a disease linked to a dysregulation of the activity of at least one kallikrein, such as multiple sclerosis.

It also relates to compounds or compositions according to the invention, for use as medicaments, in particular for treating neurodegenerative diseases, such as multiple sclerosis.

It also relates to a method for treating a disorder or a disease linked to a dysregulation of the activity of at least one kallikrein of a subject, comprising the administration to said subject of at least one compound of formula (I) or a composition comprising said compound.

DETAILED DESCRIPTION OF THE INVENTION

The present invention relates to compounds of formula (I) as defined above, for use in the treatment of a disorder or a disease linked to a dysregulation of the activity of at least one kallikrein.

According to the present invention, the term "alkyl" denotes a halogenated or non-halogenated, linear, branched or cyclic, saturated hydrocarbon-based radical having more particularly from 1 to 6, preferably 1 to 4, carbon atoms. Thus, among the alkyl radicals, mention may in particular be made of the methyl, ethyl, propyl, isopropyl, cyclopropyl, butyl, isobutyl, tert-butyl, pentyl, neopentyl, n-hexyl or cyclohexyl radical. Groups comprising one or two carbon atoms or comprising from 1 to 4 carbon atoms are particularly preferred. The methyl and ethyl groups are most particularly preferred. The alkyl radicals may be halogenated, and in particular perhalogenated, such as $CF_3$.

The term "alkyloxy" or "alkoxy" refers to an alkyl chain bonded to the rest of the molecule by means of an oxygen atom. The alkyl chain corresponds to the definition stated above.

According to one particular embodiment, the compounds are of formula (I) wherein $R_5$ represents an alkyl radical having from 1 to 6, preferably 1 to 4, carbon atoms. Preferably, $R_5$ is chosen from a methyl, ethyl, n-propyl, isopropyl, n-butyl and tert-butyl radical, in particular a methyl radical.

According to another particular embodiment, $R_5$ and $R_6$ together form a ring with the two adjacent carbons of the phenyl ring to which they are attached, so as to form a naphthyl group, optionally substituted with at least one halogen atom, or an OH, $(C_1-C_6)$alkyl, $(C_1-C_6)$alkoxy, —$C(O)_2R$, or —$N(R)C(O)R'$ radical, wherein R and R' are independently H or $(C_1-C_6)$alkyl, preferably at least one $(C_1-C_6)$alkyl or $(C_1-C_6)$alkoxy radical or a halogen atom.

The terms "alkyl" and "alkoxy" are as defined above.

The term "halogen atom" is intended to mean a chlorine, fluorine, bromine or iodine atom.

According to another particular embodiment, the compound of formula (I) has an amino protective group on the amine function.

The term "amino protective group" is intended to mean a group of the type of those used in peptide synthesis, such as, for example, acyl groups, for instance formyl, acetyl, propionyl, phenylacetyl, phenoxyacetyl, etc.; an alkoxycarbonyl group, such as tert-butoxycarbonyl (BOC), etc.; an alkoxyalkylcarbonyl group, such as methoxypropionyl, etc.; a substituted alkoxycarbonyl group, such as trichloroethoxycarbonyl, etc.; a substituted alkylcarbonyl group, such as monochloromethylcarbonyl, monochloroethylcarbonyl, dichloromethylcarbonyl, trichloromethylcarbonyl, trichloroethylcarbonyl, trichloropropylcarbonyl, trifluoromethylcarbonyl, etc.; an arylalkoxycarbonyl group, such as benzyloxycarbonyl, etc.; a substituted arylalkoxycarbonyl group, such as 4-nitrobenzyloxycarbonyl, etc.; a benzyl group, optionally substituted with at least one $(C_1-C_6)$alkyl or $(C_1-C_6)$alkoxy radical or a halogen atom; an optionally substituted diphenylmethyl group; an optionally substituted trityl group, such as 4-methoxyphenyldiphenylmethyl or di(4-methoxyphenyl)phenylmethyl.

The compounds of formula (I) also comprise the optical and geometric isomers, the racemates, the tautomers, the salts, the hydrates and the mixtures of the compounds according to the invention.

The compounds of formula (I) include the pharmaceutically acceptable salts, in particular the inorganic and organic acid salts. Representative examples of inorganic acids include hydrochloric acid, hydrobromic acid, iodic acid, phosphoric acid, etc. Representative examples of organic acids include formic acid, acetic acid, trichloroacetic acid, trifluoroacetic acid, propionic acid, benzoic acid, cinnamic acid, citric acid, fumaric acid, maleic acid, methanesulfonic acid, etc. Other organic or inorganic acid addition salts include the pharmaceutically acceptable salts described in J. Pharm. Sci. 1977, 66, 2, and in the "Handbook of Pharmaceutical Salts: Properties, Selection, and Use" edited by P. Heinrich Stahl and Camille G. Wermuth 2002. According to one particular embodiment, the salts are chosen from the maleate, hydrochloride, hydrobromide and methanesulfonate.

According to one particular embodiment, the compound used according to the present invention is chosen from:
N-(4-(aminomethyl)phenyl)-1-hydroxy-2-naphthamide,
N-(4-(aminomethyl)phenyl)-3-hydroxy-2-naphthamide,
N-(4-(aminomethyl)phenyl)-4-methyl-2-hydroxybenzamide,
N-(4-(aminomethyl)phenyl)-6-methoxy-1-hydroxy-2-naphthamide,
N-(4-(aminomethyl)phenyl)-4-isopropyl-2-hydroxybenzamide,
and a salt thereof, in particular the hydrochloride, or an amino-protected compound thereof.

According to a more specific embodiment, the compound used is chosen from N-(4-(aminomethyl)phenyl)-1-hydroxy-2-naphthamide, N-(4-(aminomethyl)phenyl)-4-methyl-2-hydroxybenzamide, a salt thereof, in particular the hydrochloride or an amino-protected compound thereof.

Another subject of the invention is the N-(4-(aminomethyl)phenyl)-4-isopropyl-2-hydroxybenzamide compound, a salt thereof, in particular the hydrochloride, or an amino-protected compound thereof.

Another subject of the present invention relates to a pharmaceutical composition comprising, in a pharmaceutically acceptable support, at least one compound of formula (I) as described above, optionally in combination with another therapeutic active agent.

According to one particular embodiment, a pharmaceutical composition comprising, in a pharmaceutically acceptable support, at least one compound of formula (I) chosen from:
N-(4-(aminomethyl)phenyl)-1-hydroxy-2-naphthamide,
N-(4-(aminomethyl)phenyl)-3-hydroxy-2-naphthamide,
N-(4-(aminomethyl)phenyl)-4-methyl-2-hydroxybenzamide, N-(4-(aminomethyl)phenyl)-6-methoxy-1-hydroxy-2-naphthamide, N-(4-(aminomethyl)phenyl)-4-isopropyl-2-hydroxybenzamide, and a salt thereof, in particular the hydrochloride, or an amino-protected compound thereof.

In particular, the pharmaceutical composition comprises the compound chosen from N-(4-(aminomethyl)phenyl)-1-hydroxy-2-naphthamide and N-(4-(aminomethyl)phenyl)-4-methyl-2-hydroxybenzamide, more specifically N-(4-(aminomethyl)phenyl)-4-isopropyl-2-hydroxybenzamide.

The invention also relates to the use of a compound as defined above, for preparing a pharmaceutical composition intended for the implementation of a method for treating the human or animal body.

The term "pharmaceutically acceptable support" is intended to mean any support (for example excipient, substance, solvent, etc.) which does not interfere with the efficacy of the biological activity of the therapeutic active agent(s) present and which is not toxic to the subject to whom the composition is administered. The pharmaceutical compositions according to the invention advantageously comprise one or more pharmaceutically acceptable excipients or carriers. Mention may for example be made of physiological, isotonic, buffered, etc., saline solutions, compatible with a pharmaceutical use and known to those skilled in the art. The compositions may contain one or more agents or carriers chosen from dispersants, solubilizers, stabilizers, preservatives, solvents, etc.

The compounds or compositions according to the invention can be administered in various ways and in various forms. Thus, they can be injected orally or systemically, such as for example intravenously, intramuscularly, subcutaneously, transdermally, intra-arterially, etc. For injections, the compounds are generally conditioned in the form of liquid suspensions, which can be injected by means of syringes or drips, for example. It is understood that the flow rate and/or the dose injected can be adjusted by those skilled in the art as a function of the patient, the pathological condition, the method of administration, etc. Typically, the compounds are administered at doses that can range between 1 µg and 2 g/administration, preferentially from 0.1 mg to 1 g/administration. The administrations can be daily or repeated several times a day, as appropriate.

Furthermore, the composition according to the invention can also comprise at least one other therapeutic active principle or agent. The pharmaceutical composition according to the invention is more specifically for simultaneous, separate or sequential use or administration of the compound according to the invention and of at least one other therapeutic active principle or agent, in particular for the treatment of a disorder or a disease linked to a dysregulation of the activity of at least one kallikrein, and in particular kallikrein 6.

It advantageously involves a compound or a pharmaceutical composition according to the invention for the treatment of a disorder or a disease linked to a dysregulation of the activity of at least one kallikrein, and in particular kallikrein 6. It has been found, surprisingly, that the compounds of formula (I) have reversible kallikrein 6-inhibiting properties. They also have not insignificant inhibitory properties with respect to plasmin and/or tissue kallikrein (KLK1). They also have the advantage of not being neurotoxic, in particular with respect to primary neurons and oligodendrocytes.

The compound of formula (I) or the pharmaceutical composition according to the invention are particularly suitable for the treatment of inflammatory, neurodegenerative or neuroinflammatory diseases.

This involves in particular the treatment of diseases chosen from cerebral ischemia, multiple sclerosis, Parkinson's disease, Alzheimer's disease, spinal cord lesions, pulmonary inflammation, vascular complications, in particular linked to diabetes.

The other therapeutic active principle or agent is advantageously a therapeutic active principle or agent suitable for the treatment as mentioned above, and in particular that can be used for a treatment of neurodegenerative or neuroinflammatory diseases of the central nervous system, or a treatment of diseases chosen from cerebral ischemia, multiple sclerosis, Parkinson's disease, Alzheimer's disease, spinal cord lesions, pulmonary inflammation, vascular complications, in particular linked to diabetes.

According to the invention, the term "treatment" or "treating" is intended to mean an improvement of a prophylaxis of the disorder or disease, or at least a symptom thereof. This includes the improvement or prevention of at least one measurable physical parameter of the disorder or disease to be treated, which is not necessarily discernible in the subject. The terms "treatment" or "treating" also refer to the inhibition or the slowing down of the progression of the disease or of the disorder, or the stabilization of one of the symptoms of the disease or of the disorder. It may also involve the delaying of the triggering of at least one symptom of the disease or of the disorder. According to certain embodiments, the compounds of the invention are administered as a preventative measure. In this context, the terms "treatment" or "treating" refer to the reduction of the risk of developing the disease or the disorder.

FIGURES

FIG. 1: Evaluation of the neurocytotoxicity of the compounds 1 (comparative), 2 and 4 (according to the invention). The percentage cell survival was determined by measuring the absorbance at 485 nm for each concentration compared with the controls treated only with complete medium (positive control) or 20% DMSO (negative control). Each concentration was tested in quadruplicate.

Figure 2:
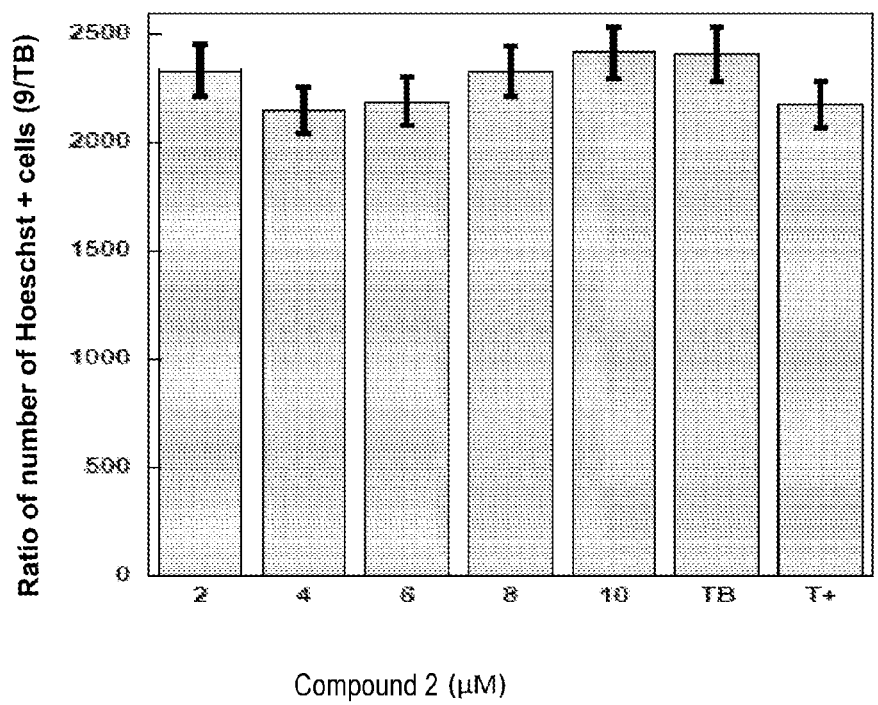
Figure 3:
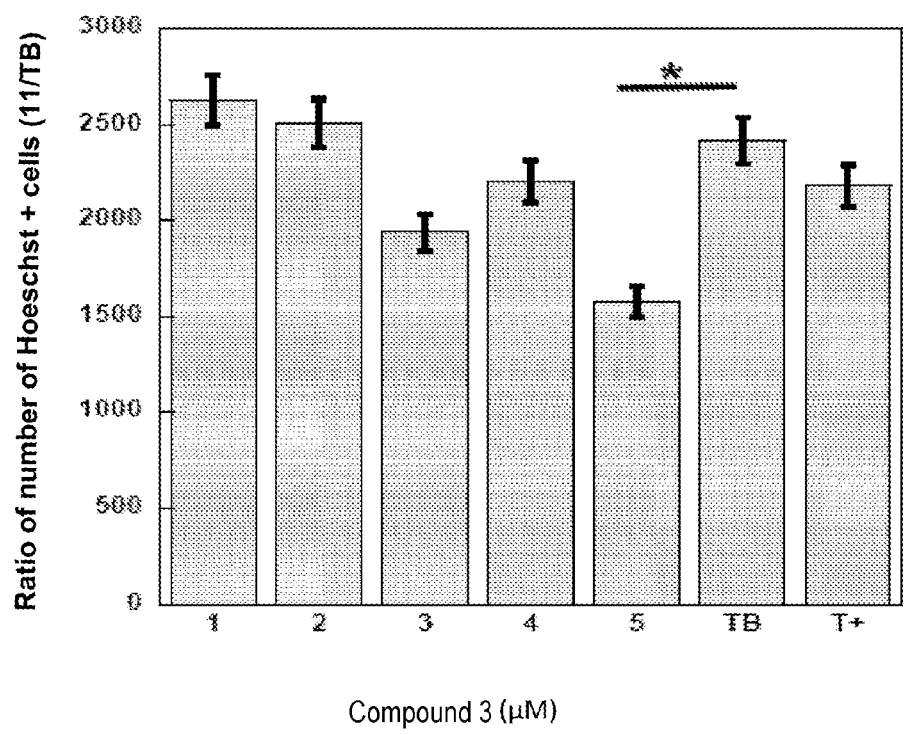
Figure 4:
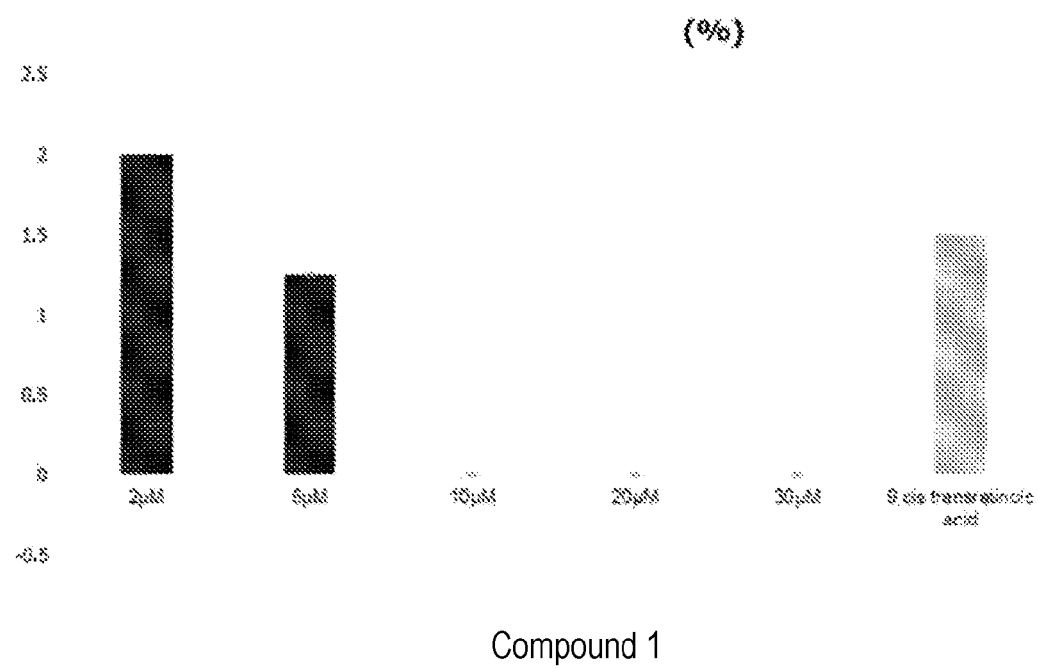
Figure 5:
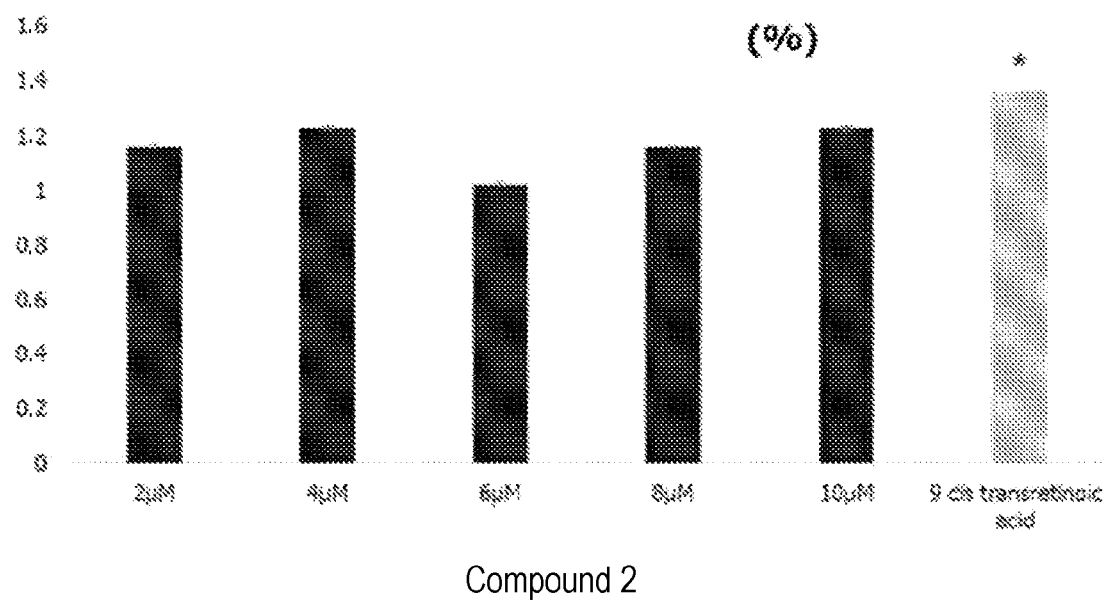
Figure 6:
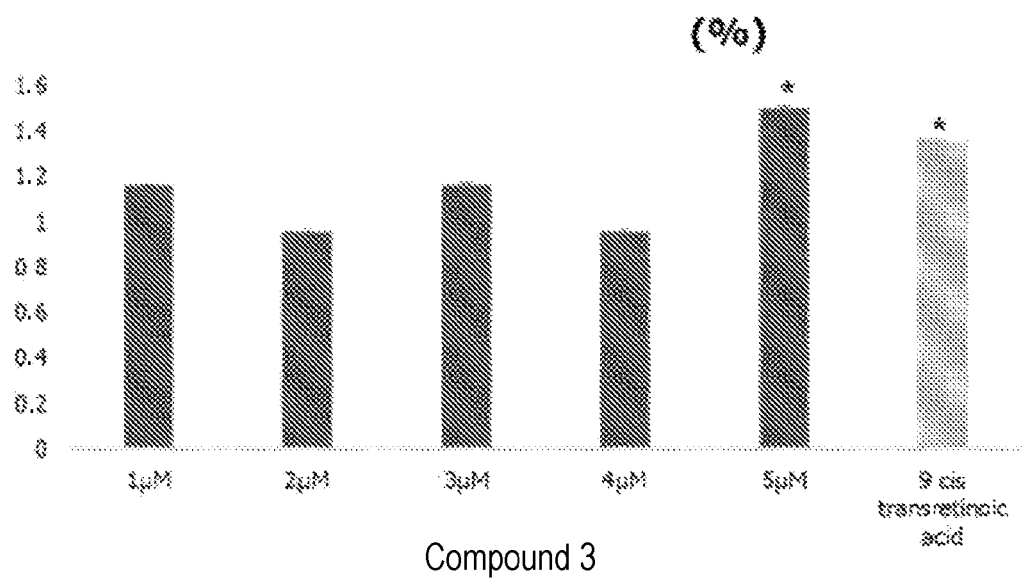
Figure 7:
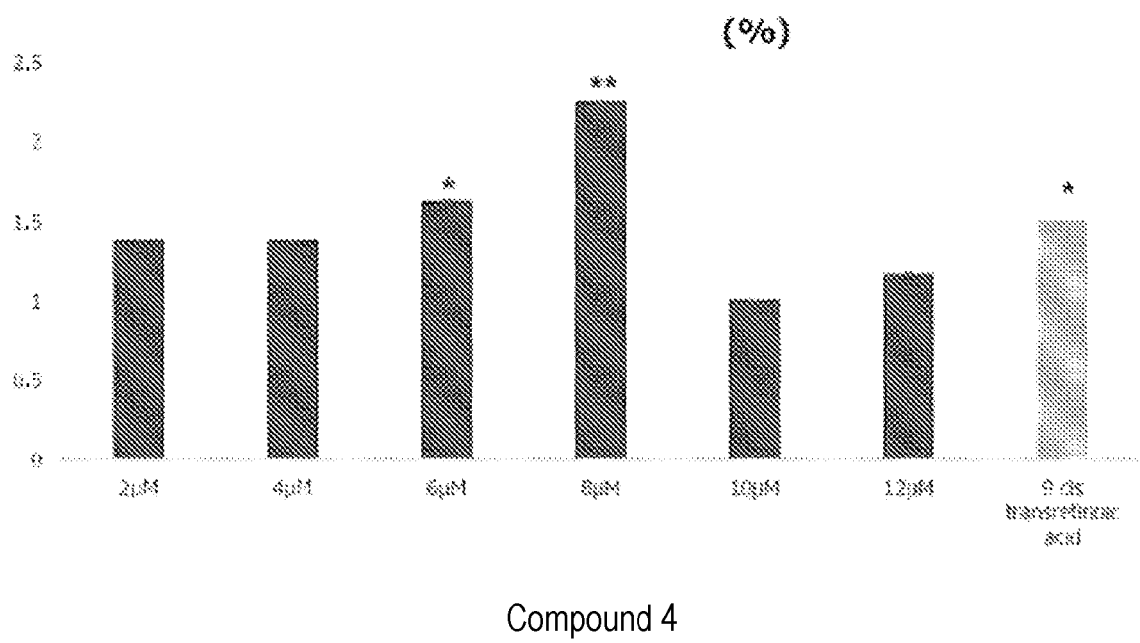

FIGS. 2 and 3: Evaluation of the cytotoxicity of the compounds 2 and 3 on the GFP/-mCherry oligodendrocyte line. The cell survival was evaluated by measuring the fluorescence intensity of the Hoechst staining compared with the basal control (TB). Each concentration was tested in quadruplicate. Statistics: Mann-Whitney test (p value=0.019). FIG. 2: Compound 2, FIG. 3: Compound 3. Legend—TB: basal control, T+: positive control (9-cis-retinoic acid).

FIGS. 4-7: Evaluation of the effect of the compounds 1 (comparative), 2, 3 and 4 on oligodendrocyte differentiation. The oligodendrocyte differentiation was evaluated by measuring the fluorescence intensity of the mCherry labeling, mCherry being a cell differentiation marker, relative to the basal control (TB). Each concentration was tested in quadruplicate. Statistics: Mann-Whitney test (p value=0.01). Legend—TB: basal control, T+: positive control (9-cis-retinoic acid).

Figure 8:
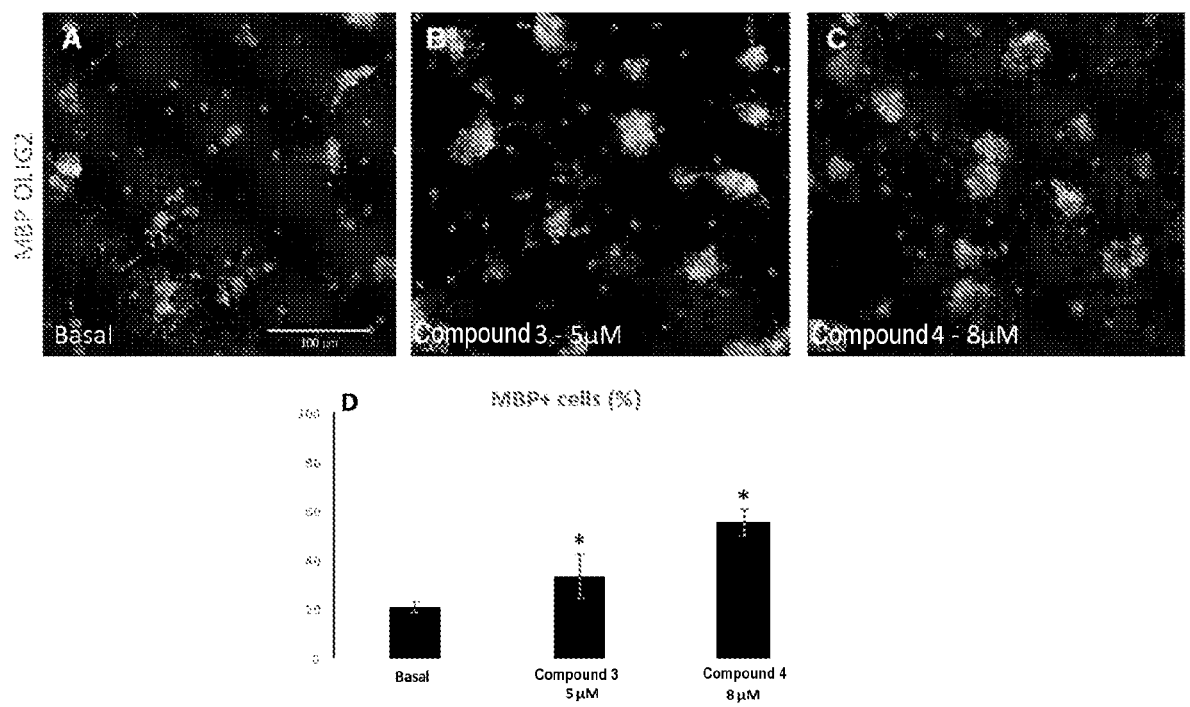

FIG. 8: Evaluation of the compounds 3 and 4 on a primary culture of rat OPCs. The cells were treated with the compounds 3 and 4 (3 µM, 4 µM, 5 µM and 4 µM, 6 µM, 8 µM respectively). After quantification of the MBP labeling (MBP+ cells) relative to the basal control (A), the compound 3 has an effect promoting OPC differentiation at 5 µM (B). The same result is observed for the compound 4 at a concentration of 8 µM (C). The percentage (%) of MBP positive cells (MBP+) after treatment with the compounds 3 (5 µM) and 4 (8 µM) relative to the basal control (D).

The invention will be understood more clearly by means of the examples which follow, which are intended to be illustrative and nonlimiting.

EXAMPLES

Example 1: Synthesis of the Compounds

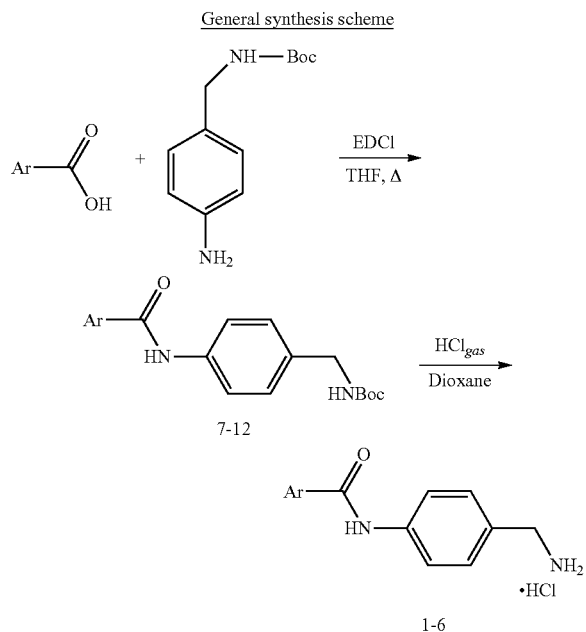

General synthesis scheme

General Procedure for the Synthesis of Compounds 7-12

103 mg of EDCI (N-(3-dimethylaminopropyl)-N'-ethyl-carbodiimide hydrochloride (0.45 mmol, 1 equivalent) and 1 equivalent of tert-butyl-(4-aminobenzyl)carbamate (0.45 mmol), synthesized according to the method described by V. Famiglini et al., Eur. J. Med. Chem. 2014, 80, 101-111, are added to a solution of 100 mg of the appropriate carboxylic acid derivative (0.45 mmol), dissolved in 2.5 ml of THF (tetrahydrofuran). The solution is stirred, then brought to reflux for 12 hours. After a return to ambient temperature, the solution is evaporated to dryness. The residue is dissolved in 20 ml of ethyl acetate and the resulting solution is washed with a 1N (3×20 ml) aqueous hydrochloric acid solution, then with 20 ml of a saturated aqueous sodium hydrogen carbonate solution. The organic phase is dried over anhydrous sodium sulfate, filtered and then evaporated under vacuum. The residue is then purified, either by washing (2×5 ml) with diethyl ether (compound 10), or by washing (2×5 ml) with dichloromethane (compound 9), or chromatographed on silica gel for the other compounds.

Tert-butyl (4-(4-methyl-2-hydroxybenzoyl))aminobenzylcarbamate (Compound 7)

Eluent: nHex/AcOEt 1/2 v/v. Pale yellow solid (mass: 131 mg, yield: 82%); $^1$H NMR (CDCl$_3$, 400 MHz): δ ppm 1.45 (s, 9H), 2.33 (s, 3H), 4.28 (d, 2H, J=5.5 Hz), 4.84 (bs, 1H), 6.70 (dd, 1H, J=8.1 Hz, 1.1 Hz), 6.82 (d, 1H, J=1.1 Hz), 7.27 (d, 2H, J=8.4 Hz), 7.39 (d, 1H, J=8.1 Hz), 7.50 (d, 2H, J=8.4 Hz), 7.93 (bs, 1H), 11.94 (s, 1H); $^{13}$C NMR (CDCl$_3$, 100 MHz): δ ppm 21.9, 28.6, 44.4, 79.9, 112.1, 119.3, 120.3, 121.6, 125.5, 128.4, 136.1, 136.2, 146.1, 156.1, 162.1, 168.6; HPLC, Tr=1.90 min; MS (ESI+): m/z 357.2 [M+H]$^+$, 379.1 [M+Na]$^+$, 301.2 [M-tBu]$^+$ Tert-butyl (4-(1-hydroxy-2-naphthoyl))aminobenzylcarbamate (Compound 8)

Elution: nHex/AcOEt 3/1 v/v; white solid (mass: 40 mg, yield: 23%); $^1$H NMR (DMSO d6, 300 MHz): δ ppm 1.40 (s, 9H), 4.13 (d, 2H, J=5.9 Hz), 7.27 (d, 2H, J=8.1 Hz), 7.40 (bt, 1H, J=5.9 Hz), 7.46 (d, 1H, J=8.9 Hz), 7.58 (dd, 1H, J=8.1 Hz, 7.1 Hz), 7.68 (m, 3H), 7.92 (d, 1H, J=8.1 Hz), 8.10 (d, 1H, J=9.0 Hz), 8.31 (d, 1H, J=8.1 Hz), 10.92 (bs, 1H); $^{13}$C NMR (DMSO d$_6$, 75 MHz): δ ppm 28.2, 43.0, 77.8, 107.5, 117.7, 121.1, 123.0, 124.7, 125.9, 127.2, 127.5, 129.1, 136.0, 136.1, 136.7, 155.8, 160.0, 169.4; HPLC, Tr=2.13 min; MS (ESI+): m/z 415.1 [M+Na]$^+$, 337.0 [M-tBu]$^+$ Tert-butyl (4-(3-hydroxy-2-naphthoyl))aminobenzylcarbamate (Compound 9)

White solid (mass: 57 mg, yield: 32%); $^1$H NMR (DMSO d$_6$, 400 MHz): δ ppm 1.40 (s, 9H), 4.11 (d, 2H, J=6.1 Hz), 7.25 (d, 2H, J=8.4 Hz), 7.32 (s, 1H), 7.35 (m, 2H), 7.50 (ddd, 1H, J=8.4 Hz, J=6.8 Hz, J=1.0 Hz), 7.69 (d, 2H, J=8.4 Hz), 7.75 (d, 1H, J=8.2 Hz), 7.92 (d, 1H, J=8.2 Hz), 8.51 (s, 1H), 10.65 (bs, 1H); $^{13}$C NMR (DMSO d$_6$, 100 MHz): δ ppm 28.2, 43.0, 77.7, 110.6, 120.5, 121.6, 123.7, 125.7, 126.8, 127.4, 128.1, 128.7 130.4, 135.8, 135.9, 137.0, 154.0, 155.8, 165.6; HPLC, Tr=1.99 min; MS (ESI+): m/z 415.2 [M+Na]$^+$, 337.1 [M-tBu]$^+$ Tert-butyl (4-(6-methoxy-1-hydroxy-2-naphthoyl)) aminobenzylcarbamate (Compound 10)

White solid (mass: 34 mg, yield: 18%); $^1$H NMR (CDCl$_3$, 300 MHz): δ ppm 1.48 (s, 9H), 3.94 (s, 3H), 4.30 (d, 2H, J=5.4 Hz), 4.87 (bs, 1H), 7.07 (d, 1H, J=2.3 Hz), 7.16 (dd, 1H, J=9.1 Hz, 2.4 Hz), 7.20 (d, 1H, J=8.1 Hz), 7.30 (d, 2H, J=8.3 Hz), 7.44 (d, 1H, J=9.1 Hz), 7.55 (d, 2H, J=8.3 Hz), 7.98 (bs, 1H), 8.35 (d, 1H, J=9.1 Hz); $^{13}$C NMR (CDCl$_3$, 75 MHz): δ ppm 28.6, 44.4, 55.5, 79.3, 105.4, 106.2, 117.6, 118.2, 121.0, 121.6, 121.7, 125.9, 128.4, 136.0, 136.2, 138.6, 142.7, 143.1, 160.6, 161.6; HPLC, Tr=2.14 min; MS (EH: m/z 445.2 [M+Na]$^+$, 367.1 [M-tBu]$^+$ Tert-butyl (4-(5-tert-butyl-2-hydroxybenzoyl))aminobenzylcarbamate (Compound 11)

Elution: DCM/EtOH 98.5/1.5 v/v; white solid (mass: 58 mg, yield: 32%); $^1$H NMR (CDCl$_3$, 300 MHz): δ ppm 1.31 (s, 9H), 1.44 (s, 9H), 4.26 (d, 2H, J=5.9 Hz), 4.89 (bs, 1H), 6.93 (d, 1H, J=8.7 Hz), 7.24 (m, 2H), 7.48 (m, 4H), 8.24 (bs, 1H), 11.0 (s, 1H); $^{13}$C NMR (CDCl$_3$, 75 MHz): δ ppm 28.6, 31.4, 31.6, 44.4, 79.9, 114.4, 118.4, 121.9, 122.1, 128.2, 132.3, 136.0, 136.1, 142.0, 156.1, 159.3, 168.7; HPLC, Tr=2.10 min; MS (ESI+): m/z 399.3 [M+H]$^+$ Tert-butyl (4-(4-isopropyl-2-hydroxybenzoyl))aminobenzylcarbamate (Compound 12)

Elution: nHex/AcOEt 3/1 v/v; white solid (mass: 54 mg, yield: 31%); $^1$H NMR (CDCl$_3$, 300 MHz): δ ppm 1.60 (d, 6H, J=6.7 Hz), 1.83 (s, 9H), 3.24 (hept, 1H, J=6.7 Hz), 4.64 (d, 2H, J=4.0 Hz), 5.25 (bs, 1H), 7.12 (d, 1H, J=7.1 Hz), 7.60 (d, 2H, J=7.6 Hz), 7.86 (m, 3H), 8.47 (bs, 1H), 12.30 (bs, 1H); $^{13}$C NMR (CDCl$_3$, 100 MHz): δ ppm 23.7, 28.6, 34.4, 44.4, 79.9, 112.5, 116.5, 117.9, 121.7, 125.8, 128.3, 136.0, 136.2, 156.2, 156.9, 162.1, 168.6; HPLC, Tr=2.09 min; MS (ESI+): m/z 407.1 [M+Na]$^+$, 385.2 [M+H]$^+$ General Procedure for the Synthesis of Compounds 1-6

0.2 mmol of compounds 7-12 are dissolved in 5 ml of a 4N hydrochloric acid solution in 1,4-dioxane. The solution is stirred at ambient temperature for 1 hour 30. The dioxane is evaporated off under reduced pressure and the residue is washed with diethyl ether to give compounds 1-6.

N-(4-(Aminomethyl)phenyl)-5-tert-butyl-2-hydroxy-benzamide hydrochloride (Compound 1-Comparative Example)—Compound 8 Described in Liang et al. (Bioorganic & Medicinal Chemistry Letters, 22 (2012), 2450-2455)

White solid. Mass: 52 mg, yield: 73%; $^1$H NMR (DMSO d$_6$, 300 MHz): δ ppm 1.20 (s, 9H), 3.93 (d, 2H, J=5.2 Hz), 4.31 (bs, 2H), 6.81 (d, 1H, J=8.4 Hz), 7.15 (m, 3H), 7.42 (m, 3H), 8.45 (bs, 3H), 10.43 (s, 1H); $^{13}$C NMR (DMSO d$_6$, 75 MHz): δ ppm 31.4, 33.7, 41.7, 46.3, 114.7, 119.0, 120.0, 123.2, 125.8, 127.5, 130.0, 130.3, 140.9, 153.3; HPLC, Tr=1.39 min; MS (ESI+): m/z 285.2 [M+H]$^+$ N-(4-(Aminomethyl)phenyl)-1-hydroxy-2-naphth-amide hydrochloride (Compound 2)

White solid. Mass: 63 mg, quantitative yield, $^1$H NMR (DMSO d$_6$, 300 MHz): δ ppm 4.02 (s, 2H), 7.46 (d, 1H, J=8.9 Hz), 7.53 (d, 2H, J=8.3 Hz), 7.59 (d, 1H, J=7.5 Hz), 7.68 (t, 1H, J=7.5 Hz), 7.80 (d, 2H, J=8.3 Hz), 7.92 (d, 1H, J=8.0 Hz), 8.22 (d, 1H, J=8.9 Hz), 8.31 (d, 1H, J=8.3 Hz), 8.48 (bs, 3H), 10.43 (s, 1H); $^{13}$C NMR (DMSO d$_6$, 75 MHz): δ ppm 41.8, 107.5, 117.8, 122.1, 123.1, 123.2, 124.6, 125.9, 127.5, 129.2, 129.4, 130.2, 136.0, 137.8, 160.0, 169.6; HPLC, Tr=1.45 min; MS (ESI+): m/z 294.1 [M+H+1]$^+$ N-(4-(Aminomethyl)phenyl)-3-hydroxy-2-naphth-amide hydrochloride (Compound 3)

White solid. Mass: 38 mg, yield: 61%); $^1$H NMR (DMSO d$_6$, 400 MHz): δ ppm 4.00 (s, 2H), 7.37 (m, 2H), 7.51 (m, 3H), 7.76 (d, 1H, J=8.3 Hz), 7.80 (d, 2H, J=8.4 Hz), 7.94 (d, 1H, J=8.3 Hz), 8.35 (bs, 3H), 8.53 (s, 1H), 10.70 (s, 1H), 11.39 (bs, 1H); $^{13}$C NMR (DMSO d$_6$, 100 MHz): δ ppm 41.8, 110.6, 120.4, 121.8, 123.7, 125.8, 126.9, 128.1, 128.7, 129.4, 129.6, 130.6, 135.8, 138.7, 153.6, 165.6; HPLC, Tr=1.26 min; MS (ESI+): m/z 294.2 [M+H+1]$^+$ N-(4-(Aminomethyl)phenyl)-4-methyl-2-hydroxy-benzamide hydrochloride (Compound 4)

Beige solid (mass: 53 mg, yield: 90%); $^1$H NMR (DMSO d$_6$, 400 MHz): δ ppm 2.30 (s, 3H), 3.98 (q, 2H, J=5.6 Hz), 6.78 (d, 1H, J=8.2 Hz), 6.84 (s, 1H), 7.48 (d, 2H, J=8.4 Hz), 7.74 (d, 2H, J=8.4 Hz), 7.94 (d, 1H, J=8.2 Hz), 8.43 (bs, 3H), 10.46 (s, 1H); $^{13}$C NMR (DMSO d$_6$, 100 MHz): δ ppm 21.1, 41.8, 114.2, 117.5, 120.1, 120.9, 129.0, 129.5, 130.3, 138.3, 144.4, 158.8, 166.7; HPLC, Tr=1.11 min; MS (ESI+): m/z 258.0 [M+H+1]$^+$ N-(4-(Aminomethyl)phenyl)-6-methoxy-1-hydroxy-2-naphthamide hydrochloride (Compound 5)

Beige solid (mass: 65 mg, yield: 91%); $^1$H NMR (DMSO d$_6$, 300 MHz): δ ppm 3.91 (s, 3H), 4.02 (s, 2H), 7.19 (dd, 1H, J=9.2, 2.5 Hz), 7.35 (m, 2H), 7.51 (d, 2H, J=8.6 Hz), 7.77 (d, 2H, J=8.6 Hz), 8.14 (d, 1H, J=9.2 Hz), 8.20 (d, 1H, J=9.2 Hz), 8.36 (bs, 3H), 10.55 (bs, 1H), 14.00 (s, 1H); $^{13}$C NMR (DMSO d$_6$, 75 MHz): δ ppm 41.8, 55.4, 105.7, 106.4, 117.0, 117.9, 119.4, 122.0, 123.9, 125.0, 129.4, 130.1, 137.9, 138.1, 159.9, 160.3, 169.7; HPLC, Tr=1.36 min; MS (ESI+): m/z 324.2 [M+H]$^+$ N-(4-(Aminomethyl)phenyl)-4-isopropyl-2-hydroxy-benzamide hydrochloride (Compound 6)

White solid (mass: 41 mg, yield: 56%); $^1$H NMR (DMSO d$_6$, 400 MHz): δ ppm 1.20 (d, 6H, J=6.8 Hz), 2.87 (hept, 1H, J=6.8 Hz), 3.99 (d, 2H, J=3.9 Hz), 6.87 (m, 2H), 7.48 (d, 2H, J=8.3 Hz), 7.74 (d, 2H, J=8.3 Hz), 7.95 (d, 1H, J=7.9 Hz), 8.39 (bs, 3H), 10.5 (s, 1H), 11.97 (bs, 1H); $^{13}$C NMR (DMSO d$_6$, 100 MHz): δ ppm 23.3, 33.3, 41.8, 114.6, 114.7, 117.4, 120.8, 129.0, 129.4, 138.3, 155.0, 158.8, 166.7; HPLC, Tr=1.33 min; MS (ESI$^+$): m/z 286.1 [M+H+1]$^+$ Example 2: Studies of the Compounds—Activities on KLK6, KLK1 and Plasmin The common point between kallikrein 6 (KLK6), plasmin and tissue kallikrein (KLK1) is their capacity to activate PAR receptors (Protease Activated Receptors) by cleaving the N-terminal portion of the latter. The PAR receptors, in particular the PAR1 and PAR2 receptors, are known to be expressed in immune cells. Thus, the uncontrolled activation of said receptors contributes to inflammatory processes.

Materials and Methods

1. Experimental Procedure

A miniaturized test was developed for each protease studied. The conditions used for the molecule screenings in 96-well plates allow good reproducibility of the activity measurements on very small volumes using the buffer 50 mM Tris-HCl, 1 M sodium citrate, 0.05% (v/v) Brij-35 and the fluorogenic peptide substrates Boc-VPR-AMC, Boc-QAR-AMC and Boc-PFR-AMC at 37° C. and at pH 7.0.

In a typical test, 100 µl of reaction medium contains the buffer, 1 µl of recombinant enzyme, 1 µl of substrate and 1 µl of the compound tested at 10 µM (in the control, 1 µl of DMSO). In each well, the inhibitor is deposited in the presence of the enzyme-buffer mixture for preincubation for 15 minutes at 37° C. The enzymatic reaction is then triggered by adding the buffer-substrate mixture (100 µM). The release of the 7-amino-4-methylcoumarin fluorescent group (AMC, $\lambda_{ex}$=360 nm, $\lambda_{em}$=460 nm) following the hydrolysis of the substrate catalyzed by the enzyme is monitored for 30 minutes at 37° C. using a FLUOstar spectrofluorimeter.

Other FRET fluorogenic substrates which mimic the N$_{ter}$ portion of G protein-coupled protease-activated receptors (PARs) were used for KLK6 (PAR-2) and plasmin (PAR-4) under the same conditions, using the wavelengths ($\lambda_{ex}$=320 nm, $\lambda_{em}$=405 nm).

TABLE 1

| Protease | Substrate (100 μM) | Buffer |
|---|---|---|
| KLK1: 1.6 nM | Boc-PFR-↓AMC | Tris-HCl 50 mM, CaCl$_2$ 10 mM, NaCl 150 mM, Brij-35 0.05%, pH 7.5 |
| KLK6: 2 nM/10 nM | Boc-QAR-↓AMC/ PAR-2 (Abz-SSKGR↓SLIGQ-EDDnp) | Tris-HCl 50 mM, Citrate 1M, Brij-35 0.05%, pH 7 |
| Plasmin: 2.6 nM/ | Boc-QAR-↓AMC/ PAR-4 (Abz-LPAPR↓GYPGQ-EDDnp) | Tris-HCl 50 mM, Citrate 1M, Brij-35 0.05%, pH 7 |

The fluorogenic substrates Boc-QAR-AMC and Boc-PFR-AMC were purchased from the company Bachem®. The FRET substrates MBP1 (Abz-RPSQR↓HATQ-EDDnp), MBP2 (Abz-HPAR↓TAHQ-EDDnp), MBP3 (Abz-YGGR↓ASDQ-EDDnp), PAR2 (Abz-SSKGR↓SLIGQ-EDDnp) and PAR4 (Abz-LPAPR↓GYPGQ-EDDnp) were purchased from GL Biochem®. The sequences of these peptide substrates reproduce the cleavage sites of the biological substrates of KLK6 (MBP, PAR2) and of plasmin (PAR4) and were synthesized to measure. All the substrates were prepared at the concentration of 10 mM or 20 mM in 100% DMSO (Sigma-Aldrich®) and stored at ambient temperature in the dark.

2. Analysis and Quantification of the Inhibitory Effects

In order to evaluate the inhibitory effect of the compounds, the same experimental protocol is used, but in the presence of variable concentrations of the molecules to be tested before addition of the synthetic substrate. The molecules tested, which are in general insoluble in water, are dissolved beforehand in DMSO. The final percentage of DMSO in the measurement buffer is at most 3% (v/v) both in the control (no inhibitor) and in the presence of inhibitor, regardless of the concentration thereof. The percentage inhibition varies as a function of the inhibitor concentration according to equation 1. The adjustment of the experimental points in this equation makes it possible to determine the value of the IC$_{50}$ (concentration of inhibitor allowing 50% inhibition of the maximum enzymatic activity).

$$\% \text{ Inhibition}=100(v_0-v_i)/v_0=100\times[I]/(IC_{50}+[I]) \quad \text{(eq. 1)}$$

with $v_0$, initial rate in the absence of inhibitor and vi, initial rate in the absence of inhibitor.

In some cases, a sigmoidal variation is observed corresponding to equation 2:

$$\% \text{ Inhibition}=100(v0-vi)/v0=100\times[I]^{nH}/(IC_{50}^{nH}+[I]^{nH}) \quad \text{(eq. 2)}$$

with $n_H$, the Hill number.

The fluorescence measurements of the enzymatic activities were carried out using a BMG FLUOstar multiwell plate reader spectrofluorimeter controlled by the Optima® software.

The measurements are carried out in COSTAR flat-bottom 96-well black plates. The mathematical processing and statistical processing of the data were carried out using the Kaleidagraph® software. The pH measurements of the buffers were carried out using a METTLER TOLEDO SevenCompact™ pH-meter equipped with a thermal sensor and a calibration support.

The reversibility of the inhibitory effect was analyzed by the dilution method. This method makes it possible to distinguish an irreversible covalent inhibitor from a reversible inhibitor. The enzyme and the inhibitor (or the DMSO negative control) are incubated for 15 minutes at 37° C. to allow the formation of the enzyme-inhibitor (E-I) complex. Said complex is then diluted to $100^{th}$ in a buffer-substrate mixture and the measurement of the activity is then launched over a period of 30 minutes at 37° C. The initial rate obtained for DMSO control represents 100% of the activity and serves as a reference for the quantification of the residual activity of the enzyme in the presence of the inhibitor. The inhibitor concentration is chosen, on the basis of the IC$_{50}$ curves, in such a way that the enzyme is more than 80% inhibited before dilution so as to be sure that the effect after dilution is not due to an effect of the inhibitor on the enzyme. If, after dilution, the activity is more than 50% restored, the inhibitor is reversible.

In order to determine the type of inhibition exerted on the enzyme, the inhibitor is placed in competition with the substrate with respect to the active site of the enzyme. The inhibitor is preincubated at various concentrations (¼ IC$_{50}$; ½ IC$_{50}$; IC$_{50}$; 2 IC$_{50}$; 4 IC$_{50}$) with an enzyme-buffer mixture for 15 minutes to allow the formation of the E-I complex. The reaction is launched over a period of 30 minutes at 37° C. as soon as the buffer-substrate mixture is added. Several substrate concentrations are tested for the competitiveness experiment.

Following this experiment, the type of inhibition is determined by the Dixon method. The latter consists in plotting the straight line 1/Vi=f([I$_0$]) for each substrate concentration. These graphs make it possible to determine the type of inhibition (competitive, noncompetitive or uncompetitive) and also the inhibition constant Ki from the point of intersection of the various straight lines.

The compounds were also evaluated on plasmin and on KLK1. The buffers and AMC substrates used are presented in Table 1.

3. Results

The molecules were thus tested firstly at 10 μM in order to evaluate their inhibitory effect on the enzymatic activity of KLK6. The % inhibitions were determined from the residual activity of the hydrolysis of the Boc-QAR-AMC fluorogenic substrate (100 μM) by KLK6 (2 nM) after 15 minutes of incubation with each molecule at 10 μM. The compounds giving rise to percentage inhibitions of less than 50% are considered to be non-inhibitors. The results are presented in Table 2 below.

TABLE 2

| Compound | % Inhibition at 10 μM |
|---|---|
| 1 | 51.02 |
| 2 | 77.17 |
| 3 | 88.64 |
| 4 | 68.83 |
| 5 | 65 |
| 6 | 84.68 |

Compound 1 above (described in Liang et al., Bioorganic & Medicinal Chemistry letters, 22 (2012), 2450-2455) at 10 μM thus leads to a % inhibition of the KLK6 activity which is less than that observed for the compounds according to the invention.

The inhibitory capacities of the compounds and also their mechanism of action with respect to KLK6 were determined. The results are collated in Table 3 below.

TABLE 3

| Substrate Compound | Inhibition type | Boc-QAR-AMC IC$_{50}$ (μM) | K$_i$ (μM) | MBP3 IC$_{50}$ (μM) | PAR2 IC$_{50}$ (μM) |
|---|---|---|---|---|---|
| 1 | Competitive reversible | (9.06 ± 0.65) | 4.44 | (39.82 ± 5.00) | (21.71 ± 1.09) |
| 2 | Competitive reversible | (1.50 ± 0.13) | 2.26 | (7.89 ± 0.63) | (2.63 ± 0.14) |
| 3 | Noncompetitive reversible | (1.17 ± 0.05) | 0.79 | (2.38 ± 0.09) | (1.23 ± 0.07) |
| 4 | Noncompetitive reversible | (5.42 ± 0.35) | 1.92 | (8.34 ± 0.90) | (5.06 ± 0.91) |
| 5 | Competitive reversible | (3.74 ± 0.29) | 1 | ND | ND |
| 6 | Noncompetitive reversible | (1.56 ± 0.04) | 1.75 | ND | ND |

ND: not determined

The molecules were tested in order to evaluate their possible inhibitory effect on the enzymatic activity of KLK1. The % inhibitions were determined from the residual activity of the hydrolysis of the Boc-PFR-AMC fluorogenic substrate (100 μM) by KLK1 (1.6 nM) after 15 minutes of incubation at 37° C. with each molecule at 10 μM. The results are presented in Table 4 below; all the inhibitors are reversible.

TABLE 4

| Compound | % Inhibition at 10 μM | IC$_{50}$ (μM) |
|---|---|---|
| 1 | 32.83 | ni |
| 2 | 47.71 | ni |
| 3 | 77.04 | (5.90 ± 0.37) |
| 4 | 61.66 | (39.27 ± 12.07) |
| 5 | 46.53 | (30.68 ± 4.75) |
| 6 | 57.66 | (8.44 ± 0.28) |

"ni" non-inhibitor

The selectivity of the compounds with respect to plasmin was evaluated. The % inhibitions were determined from the residual activity of the hydrolysis of the Boc-QAR-AMC fluorogenic substrate (100 μM) by plasmin (2.6 nM) after 15 minutes of incubation at 37° C. with each molecule at 10 μM. The results are presented in Table 5 below.

TABLE 5

| Compound | % Inhibition at 10 μM |
|---|---|
| 1 | 39.26 |
| 2 | 97.37 |
| 3 | 80.98 |
| 4 | 54.30 |
| 5 | 100 |
| 6 | 70.15 |

The inhibitory capacities and mechanisms of inhibition of these compounds with respect to plasmin were subsequently determined. The results are collated in Table 6 below.

TABLE 6

| Substrate Compound | Inhibition type | Boc-QAR-AMC IC$_{50}$ (μM) | K$_i$ (μM) | PAR4 IC$_{50}$ (μM) |
|---|---|---|---|---|
| 1 | Competitive reversible | (17.05 ± 1.56) | 14.4 | ni |
| 2 | Competitive reversible | (1.50 ± 0.13) | 1.51 | (4.92 ± 0.54) |
| 3 | Competitive reversible | (3.75 ± 0.11) | 1.32 | (3.25 ± 0.48) |
| 4 | Competitive reversible | (12.49 ± 0.34) | 4.66 | ni |
| 5 | Noncompetitive reversible | (2.72 ± 0.34) | 2.16 | ND |
| 6 | Competitive reversible | (4.78 ± 0.23) | 0.67 | ND |

ND: not determined,
"ni" non-inhibitor

CONCLUSION

The compounds according to the invention therefore effectively and reversibly inhibit KLK6; some compounds also inhibit plasmin and/or KLK1.

Example 3: Biological Evaluations of the Compounds—Studies on Primary Cultures of Murine Cortical Neurons and on the mCherry Rat Oligodendrocyte Line Materials and Methods 1—Analysis of the Cytotoxicity on a Primary Culture of Murine Cortical Neurons The neurons were taken from the stage E16 embryos of Swiss females. The cells are seeded at a density of 50 000 cells/well in precoated sterile transparent 96-well plates. The cells are cultured for 48 h in DMEM medium supplemented with 10% fetal calf serum (FCS), penicillin, streptomycin, N2 and B27, at 37° C. under a humid atmosphere with 5% $CO_2$. The cells are then placed in the presence of the compounds described above (10, 25 or 50 μM) or of the DMSO control, and then incubated for 48 h. The medium is then replaced with 100 μl of XTT (0.3 mg·ml$^{-1}$) in order to carry out the cell viability test. XTT is a tetrazolium salt derivative, the reduction of which by the mitochondrial dehydrogenases of viable cells reveals an orangey-yellow coloration. The activity of the mitochondria is determined by measuring the absorbance at 485 nm. The percentage cell survival is calculated by the ratio of the absorbance in the presence of the inhibitor relative to the control condition (DMSO). The molecule is considered to be cytotoxic when the percentage cell survival is less than 80%.

2—Evaluation of the Effect of the Compounds on Oligodendrocyte Differentiation

The line used is a CG4 cell line, said cell line being rat oligodendrocyte precursor cells (OPCs), and doubly transduced with the GFP gene under the control of the CMV promoter and the mCherry marker gene under the control of a promoter specific for differentiated and mature oligodendrocytes. The mCherry marker is expressed only at the differentiated oligodendrocyte stage and thus makes it possible to test compounds capable of inducing OPC differentiation. The cells were also stained with Hoechst in order to evaluate their viability. The cells are cultured in the proliferation medium described by Louis et al. (Louis et al., J Neurosci Res. 1992 January; 31(1):193-204) during their seeding, and then transferred into a differentiation medium (DMEM/F12, B27, N1, biotin, laminin). The cells are treated with various concentrations of inhibitor for 72 h in 96-well plates, then screened by means of an automated inverted microscope. The experimental controls used are a basal control containing only the differentiation medium and a positive control, 9-cis-retinoic acid, which is known for its effect in inducing OPC differentiation (Huang et al., Nature Neuroscience 14, 45-53 (2011)).

Firstly, the cytotoxicity of the compounds is evaluated by virtue of the comparison of the intensity of the Hoechst staining for each experimental condition with respect to the basal control. A cytotoxic effect is assumed when this intensity significantly decreases.

Subsequently, the effect of the compounds on OPC differentiation is evaluated. For that, the intensity of the mCherry labeling is quantified for each experimental condition with respect to the basal control. A favorable effect on differentiation results in a significant increase in the mCherry fluorescence, which is the opposite to an unfavorable effect on differentiation. The results are analyzed using the Mann-Whitney statistical test.

Results

The results are presented in FIGS. 1-7.

The neurocytotoxicity of compounds 1, 2 and 4 at 10, 25 and 50 µM was evaluated on a primary culture of murine cortical neurons (FIG. 1). According to the XTT cell survival test, compounds 1 (comparative), 2 and 4 (compounds according to the invention) prove to be noncytotoxic at a concentration of 10 µM (% cell survival >80%). At a concentration of 25 µM, only compounds 2 and 4 do not induce neurocytotoxicity (% cell survival >90%). At a concentration of 25 µM, only compound 2 is not neurocytotoxic (% cell survival >90%). Regardless of the concentration used, the percentage cell survival after treatment with compounds 2 and 4 is greater than that observed with the reference compound 1. The neurocytotoxicity induced by compound 1 follows a dose-dependent effect.

The cytotoxicity was evaluated on the oligodendrocyte line doubly transduced with GFP and the mCherry labeling by quantification of the Hoechst staining. More specifically, the intensity of relative staining at each inhibitor concentration was standardized relative to that of the basal control. The results are presented in FIGS. 2 and 3, for compounds 2 and 3, respectively. When the cells are treated with compound 2 (FIG. 2), no difference in staining is observed. Thus, compound 2 is not cytotoxic. Compound 3 (FIG. 3) for its part induces a decrease in Hoechst staining relative to the basal control at 5 µM, reflecting potential cytotoxicity. An evaluation of the cytotoxicity was also carried out for compounds 1 and 4. The reference compound 1 exhibits toxicity at concentrations above 10 µM. Compound 4 does not exhibit any toxicity between 2 and 12 µM.

The effect of compounds 1, 2, 3 and 4 on oligodendrocyte differentiation was evaluated on the same cell line (FIGS. 4-7, respectively). More specifically, this effect was determined by quantification of the mCherry labeling intensity for each experimental condition relative to that of the basal control. The treatment with compound 2 induces no modification of the mCherry labeling, regardless of the concentration. This inhibitor does not therefore appear to have any effect on differentiation. On the other hand, for compounds 3 and 4, a significant increase in mCherry labeling relative to the basal control is observed at a concentration of 5 and 8 µM, respectively (pvalue=0.01, Mann-Whitney test). Compounds 3 and 4 therefore promote OPC differentiation into mature oligodendrocytes.

KLK6 plays a role on the dynamics of the differentiation of OPCs (oligodendrocyte precursor cells). OPCs follow a maturation process at the end of which they reach the final mature myelinating oligodendrocyte stage. Excess KLK6 has a dual action on these cells. On the one hand, it induces a drastic reduction in oligodendrocyte arborescence, on the other hand, it induces a slowing down of the OPC maturation process, significantly decreasing the number of mature myelinating oligodendrocytes. Thus, in view of their pharmacological and biological profiles, compounds 3 and 4, according to the invention, appear to be particularly suitable for the treatment of disorders or diseases as defined previously.

Example 4: Biological Evaluations of Compounds 3 and 4—Studies on Primary Cultures of Rat Oligodendrocyte Precursor Cells (OPCs)

Materials and Methods

Primary cultures of glial cells are obtained from rat brains at P0/P1. After having sacrificed the animals and removed the meninges, the cerebral hemispheres are enzymatically dissociated using 0.25% trypsin for 5 minutes. After inactivation of the trypsin using DMEM+10% fetal calf serum (FCS)/+1% penicillin-streptomycin and mechanical dissociation until homogenization is obtained, the cell suspension thus obtained is filtered using a 70 µm sieve. The cells are then placed in culture flasks coated with polyornithine substrate (100 µg/ml), containing a DMEM medium+10% fetal calf serum (FCS)/1% penicillin-streptomycin. The flasks are placed in an incubator (37° C., 5% $CO_2$). The medium is renewed on the fourth day of culture, then every two days for 10 to 14 days.

Secondary cultures of oligodendrocytes are obtained from these cultures after two agitation steps (250 rpm, 37° C.). The first agitation step for one hour makes it possible to remove the microglial cells, while the second agitation for 18 hours makes it possible to detach the oligodendrocyte progenitor cells (OPCs) from the astrocyte layer. The supernatant containing the cells is subsequently subjected to preferential adhesion steps in order to remove the microglial cells and also the astrocytes that could compromise the purity of the culture.

The purified OPCs are seeded onto a polyornithine substrate at 100 μg/ml at the density of 1000 cells/cm². After adhesion, the cells are left for 12 hours in a DMEM/F12 medium+2% B-27, 1% penicillin-streptomycin, bFGF (25 ng/ml) and PDGF-BB (10 ng/ml).

These same cells are then placed under differentiation for four days in a DMEM/F12 medium+2% B-27 in the presence or absence of the various molecules to be tested.

Results

Compounds 3 and 4 were evaluated on a primary culture of rat OPCs. In this model, the degree of differentiation was measured by quantifying the MBP marker. MBP, or Myelin Basic Protein, is the main constituent of myelin. MBP is expressed only by oligodendrocytes which have reached a terminal maturation stage and which therefore have acquired their myelinating property. The results are presented in FIG. 8.

The cells were treated with compounds 3 and 4 (3 μM, 4 μM, 5 μM and 4 μM, 6 μM, 8 μM respectively). After quantification of the MBP marker (MBP+ cells) relative to the basal control (A), compound 3 has a favorable effect on OPC differentiation at 5 μM (B). The same result is observed for compound 4 at a concentration of 8 μM (C). The percentage (%) of MBP positive (MBP+) cells after treatment with compounds 3 (5 μM) and 4 (8 μM) relative to the basal control (D).

Compounds 3 and 4 significantly promote OPC differentiation at concentrations of 5 μM and 8 μM respectively. These results underline the promyelinating potential of these compounds.

The invention claimed is:

1. A method for the treatment of a disorder or a disease linked to a dysregulation of the activity of at least one kallikrein of a subject in need thereof, comprising administering to said subject at least one compound of formula (I) or a composition comprising said compound, said compound being of formula (I) below:

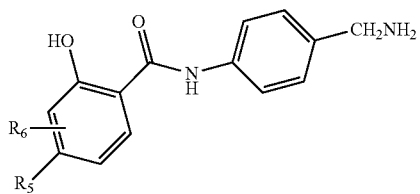

(I)

wherein:
$R_5$ represents a $(C_1-C_6)$alkyl radical and $R_6$ represents a hydrogen atom;
alternatively, $R_5$ and $R_6$ together form a ring with the two carbons of the phenyl ring to which they are attached, so as to form a naphthyl group, optionally substituted with at least one halogen atom, or an OH, $(C_1-C_6)$alkyl, $(C_1-C_6)$alkoxy, —C(O)$_2$R or —N(R)C(O)R' radical, wherein R and R' are independently a hydrogen atom or a $(C_1-C_6)$alkyl radical or a $(C_1-C_6)$alkoxy radical or a halogen atom,
the compound of formula (I) optionally having an amino protective group used in peptide synthesis, or a pharmaceutically acceptable salt of the compound of formula (I).

2. The method as claimed in claim 1, wherein $R_5$ represents an alkyl radical.

3. The method as claimed in claim 1, wherein the compound is selected from:
N-(4-(aminomethyl)phenyl)-1-hydroxy-2-naphthamide,
N-(4-(aminomethyl)phenyl)-3-hydroxy-2-naphthamide,
N-(4-(aminomethyl)phenyl)-4-methyl-2-hydroxybenzamide,
N-(4-(aminomethyl)phenyl)-6-methoxy-1-hydroxy-2-naphthamide,
N-(4-(aminomethyl)phenyl)-4-isopropyl-2-hydroxybenzamide, and a salt thereof or an amino-protected compound thereof.

4. The method as claimed in claim 1, wherein the compound is N-(4-(aminomethyl)phenyl)-1-hydroxy-2-naphthamide, N-(4-(aminomethyl)phenyl)-4-methyl-2-hydroxybenzamide, a salt thereof or an amino-protected compound thereof.

5. The method as claimed in claim 1, wherein the treatment is the treatment of inflammatory, neurodegenerative or neuroinflammatory diseases of the central nervous system.

6. The method as claimed in claim 1, wherein the treatment is the treatment of a disease selected from cerebral ischemia, multiple sclerosis, Parkinson's disease, Alzheimer's disease, spinal cord lesions, and pulmonary inflammation.

7. The method as claimed in claim 1, wherein the treatment is the treatment of multiple sclerosis.

8. The method as claimed in claim 2, wherein the alkyl radical is a methyl, ethyl, n-propyl, isopropyl, n-butyl or t-butyl radical.

9. An N-(4-(aminomethyl)phenyl)-4-isopropyl-2-hydroxybenzamide compound, a salt thereof or an amino-protected compound thereof.

10. A pharmaceutical composition comprising, in a pharmaceutically acceptable medium, at least one compound of the following formula (I):

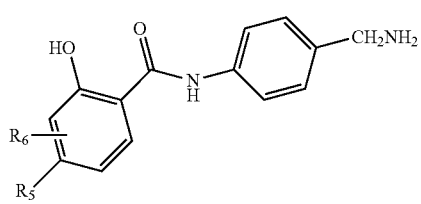

(I)

wherein:
$R_5$ represents a $(C_1-C_6)$alkyl radical and $R_6$ represents a hydrogen atom;
alternatively, $R_5$ and $R_6$ together form a ring with the two carbons of the phenyl ring to which they are attached, so as to form a naphthyl group, optionally substituted with at least one halogen atom, or an OH, $(C_1-C_6)$alkyl, $(C_1-C_6)$alkoxy, —C(O)$_2$R or —N(R)C(O)R' radical, wherein R and R' are independently a hydrogen atom or a $(C_1-C_6)$alkyl radical or a $(C_1-C_6)$alkoxy radical or a halogen atom,
optionally, wherein the compound of formula (I) has an amino protective group or a pharmaceutically acceptable salt of the compound of formula (I).

11. The composition as claimed in claim 10, wherein the compound of formula (I) is selected from:
N-(4-(aminomethyl)phenyl)-1-hydroxy-2-naphthamide,
N-(4-(aminomethyl)phenyl)-3-hydroxy-2-naphthamide, N-(4-(aminomethyl)phenyl)-4-methyl-2-hydroxybenzamide, N-(4-(aminomethyl)phenyl)-6-methoxy-1-hydroxy-2-naphthamide, N-(4-(aminomethyl)phenyl)-4-isopropyl-2-hydroxybenzamide, a salt thereof or an amino-protected compound thereof.

12. The composition as claimed in claim 10, wherein the compound is selected from N-(4-(aminomethyl)phenyl)-1-hydroxy-2-naphthamide and N-(4-(aminomethyl)phenyl)-4-methyl-2-hydroxybenzamide.

* * * * *